United States Patent [19]

Freeman

[11] Patent Number: 4,655,565
[45] Date of Patent: Apr. 7, 1987

[54] OPHTHALMIC LENSES WITH DIFFRACTIVE POWER

[75] Inventor: Michael H. Freeman, Denbigh, Wales

[73] Assignee: Pilkington P.E. Limited, United Kingdom

[21] Appl. No.: 701,134

[22] Filed: Feb. 13, 1985

Related U.S. Application Data

[63] Continuation-in-part of Ser. No. 543,257, Oct. 19, 1983, Pat. No. 4,637,697, and a continuation-in-part of Ser. No. 533,993, Sep. 20, 1983, Pat. No. 4,641,934, and a continuation-in-part of Ser. No. 368,362, Apr. 14, 1982, Pat. No. 4,642,112.

[30] Foreign Application Priority Data

Feb. 23, 1984 [GB] United Kingdom ............... 8404817

[51] Int. Cl.$^4$ .......................... G02C 7/02; G02C 7/04; G02C 7/06; A61F 2/16
[52] U.S. Cl. ............................... 351/159; 351/160 R; 351/161; 351/172; 623/6
[58] Field of Search .......................... 350/162.16, 452; 351/159, 160 R, 160 H, 161, 162, 168–172; 623/6

[56] References Cited

U.S. PATENT DOCUMENTS 4,210,391 7/1980 Cohen .................................. 351/161
4,338,005 7/1982 Cohen ............................. 350/452 X
4,340,283 7/1982 Cohen .................................. 351/161

Primary Examiner—John K. Corbin
Assistant Examiner—Scott J. Sugarman
Attorney, Agent, or Firm—F. Eugene Davis, IV; Mark P. Stone

[57] ABSTRACT

A contact or spectacle or implant lens has positive diffractive power which introduces negative longitudinal chromatic aberration that more than counteracts, and is preferably greater than twice, the natural positive longitudinal chromatic aberration of the eye. The residual negative longitudinal chromatic aberration enables the eye/brain system to perform tasks by concentrating on the appropriate color component at the different respective distances without need to accommodate.

17 Claims, 2 Drawing Figures

OPHTHALMIC LENSES WITH DIFFRACTIVE POWER

RELATED APPLICATIONS

This application is a continuation-in-part of my previous U.S. Applications: Ser. No. 543,257 filed Oct. 19, 1983, now U.S. Pat. No. 4,637,697, entitled "Multifocal Contact Lenses Utilizing Diffraction and Refraction"; Ser. No. 533,993 filed Sept. 20, 1983, now U.S. Pat. No. 4,641,934, entitled "Ophthalmic Lens with Diffractive Power"; and Ser. No. 368,362 filed Apr. 14, 1982, now U.S. Pat. No. 4,642,112, entitled "Artificial Eye Lens".

BACKGROUND OF THE INVENTION

This invention concerns improvements in or relating to ophthalmic lenses, including in particular contact lenses and spectacle lenses.

The human eye is known to exhibit longitudinal chromatic aberration so that objects at the same distance but of different colours cannot all be sharply focussed at the same time. Thus, to effect simultaneous sharp focussing orange and red objects need to be placed farther away than a green object while blue and violet objects have to be nearer the eye than the green object. The extent of the effect is about one dioptre and there is evidence to suggest that the eye/brain system makes use of this to avoid refocussing, concentrating on the blue components of objects that are close and on the red components for distant vision.

SUMMARY OF THE INVENTION

According to the present invention there is provided an ophthalmic lens having positive diffractive power which introduces negative longitudinal chromatic aberration to an extent that more than counteracts the natural positive longitudinal chromatic aberration of the eye so as to provide in use a residual negative longitudinal chromatic aberration. This can enable the eye/brain system to perform a variety of tasks without need to adjust the eye focus (accommodate) by concentrating on the appropriate colour component at the different respective distances.

The designation of the natural longitudinal chromatic aberration as positive is a matter of convention. The opposite convention is also used by some optical designers. Most materials show higher refractive index for blue light and for a positive lens the uncorrected condition gives more positive power for blue light. The terms undercorrect and overcorrect are also used. However, throughout this specification the natural longitudinal chromatic aberration of the eye is called positive and the reverse of this negative.

Preferably the positive diffractive power is of a magnitude such that the introduced negative longitudinal chromatic aberration has an absolute value greater than twice that of the natural positive longitudinal chromatic aberration of the eye, whereby the extent of the residual negative chromatic effect is greater than that of the natural positive chromatic effect. If the extent of negative longitudinal chromatic aberration required to be introduced by the ophthalmic lens is $-D$ dioptres, then the diffractive power of the lens is preferably about $+3.4D$ dioptres ($-3.4$ being the effective dispersion or V value of diffractive optics); thus if the required extent of the introduced aberration is at least $-2$ dioptres (to give, with the eye's natural extent of $+1$ dioptre, a residual effect of at least $-1$ dioptre), then the diffractive power of the lens may be at least $+6.8$ dioptres.

A lens with positive diffractive power providing negative longitudinal chromatic aberration which more than compensates the eye's natural chromatic effect can be advantageous over a lens having negative diffractive power providing positive longitudinal chromatic aberration which adds to the eye's natural chromatic effect for the following reason. A lens with negative diffractive power requires compensating positive refracting power if the residual power is to be zero, and requires a high value of positive refractive power that more than counteracts the negative diffractive power if the patient needs the lens to have residual positive power for corrective purposes. For example, if the diffractive power is about $-6$ dioptres, the design of lens for a $+12$ dioptres aphakic patient would require about $+18$ dioptres of refractive power. A lens shaped to provide such high positive refractive power requires a large central thickness with all the attendant problems; particularly with a contact lens, discomfort for the wearer and, where relevant, low oxygen transmission. With a lens having positive diffractive power in accordance with the present invention, the refractive power if any, can be relatively low. For example, with diffractive power of about $+8$ dioptres, the design of lens for the $+12$ dioptres aphakic patient requires only $+4$ dioptres of refractive power, and the lens can be relatively thin.

An ophthalmic lens in accordance with the invention need not necessarily have any refractive power, and in particular the refractive power may be zero when the positive diffractive power has a value which equals that required by the patient for corrective purposes. However, a lens in accordance with the invention may have refractive power so that the overall, or residual, power of the lens is determined by the algebraic sum of the diffractive and refractive powers. If desired, the refractive power may be negative and of a magnitude such as to balance, or cancel, the diffractive power so that the overall or residual power is substantially zero. Alternatively, however, the relative values of the diffractive and refractive powers may be such as to provide the lens with an overall or residual power, for example to give the required corrective power for the particular eye with which the ophthalmic lens is to be used. Thus, the refractive power may be negative and of greater magnitude than the diffractive power to give a negative residual power, or may be negative but of smaller magnitude than the diffractive power to give a positive residual power, or may be positive to give a greater positive overall power.

The refractive power is preferably provided by faces which are curved as viewed in axial-section, and which may be of spherical curvature.

The diffractive power is preferably provided by a transmission hologram. The hologram may be optically generated in a surface layer of the lens or within the bulk material of the lens, or may be mechanically generated as a surface relief hologram on the lens or within the lens. The diffractive power may be provided over the full visually used area of the lens, or may be provided over part only of that area. The lens may be a contact lens which may have the diffractive power over its full visually used area. Alternatively, the lens may be a spectacle lens which may have the diffractive power over part only of the visually used area, e.g. over a part corresponding to the near or reading portion of a bifocal or progressive spectacle lens. As a further possibility the lens could be an implant lens in which case the diffractive power is preferably provided over the full visually used area of the lens.

The efficiency of diffraction is preferably more than 50% at all wavelengths across the visible spectrum and the maximum efficiency is preferably more than 70%. The difference between the maximum and minimum efficiencies across the visible spectrum is preferably less than 20%, e.g. if the maximum efficiency is nearly 100% then the minimum efficiency is preferably more than 80%.

BRIEF DESCRIPTION OF THE DRAWINGS

In order that the invention may be better understood, reference will now be made to the accompanying drawing in which.

DETAILED DESCRIPTION

Figure 1:
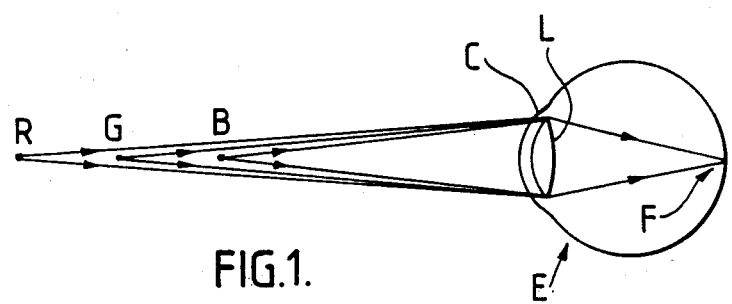
FIG. 1 is a schematic (and not to scale) representation of the chromatic viewing properties of a normal human eye.

Referring to FIG. 1, the normal human eye E has a cornea C and natural lens L by which light is focussed at F to form an image on the retina. Objects at different distances are viewed by adjusting the shape of the natural lens L (through the action of the eye muscles) so as to alter its focal length to achieve focussing at the point F of light from the respective object distance. This property of the eye is commonly known as "accommodation". However, the eye exhibits positive longitudinal chromatic aberration, which means that with the eye lens L at any one accommodation setting different colours from the same distance are not all focussed at the same point. This arises because the media of the eye have refractive indices which are slightly greater at the blue end of the spectrum than at the red end. Conversely, therefore, at any one accommodation setting, the eye can sharply focus on to the retina the image of a blue object at one distance and the image of a red object at a greater distance. This is illustrated in FIG. 1 which shows a blue object B nearer the eye and a red object R further from the eye, from both of which light is sharply focussed on the retina at F with the lens L at the same accommodation setting. Between the blue and red objects there is shown a green object G (wavelength 555 nm) whose image is also sharply focussed on to the retina at F at that particular accommodation setting. It will be understood that the distance variation is continuous through the visible spectrum and that blue, green and red objects are given as illustrative.

As a particular example of the variation at a specific accommodation setting, if in FIG. 1 the green object G is at a distance of one meter from the eye E and the eye lens L is in a state of accommodation such that (in conjunction with the action of the cornea C) an image of the green object G is sharply focussed on the retina at F, then the red object R would need to be at a distance of 2 meters from the eye E, and the blue object B would have to be at a distance of 67 cm (⅔ of a meter) from the eye E for there to be sharp focussing of the respective red and blue images on the retina at F. Thus, whereas for green light the eye has a lens power of 1 dioptre, its power in respect of red light is ½ dioptre and its power in respect of blue light in 1½ dioptres. The extent of the positive longitudinal chromatic aberration is hence about 1 dioptre, and there is evidence to suggest that the eye/brain system uses this to avoid re-focussing by concentrating on the blue components of objects that are close and on the red components for more distant vision.

Figure 2:
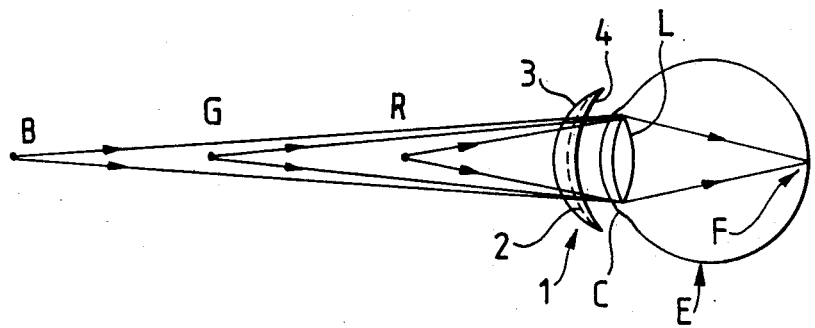
FIG. 2 is a schematic (and not to scale) representation similar to FIG. 1 but with an ophthalmic lens in accordance with the invention associated with the eye.

Referring now to FIG. 2, this shows disposed in front of the eye E an ophthalmic lens 1 which incorporates a transmission hologram 2. The hologram 2 has positive diffractive power and introduces negative longitudinal chromatic aberration to an extent that more than counteracts the natural positive longitudinal chromatic aberration of the human eye explained above with reference to FIG. 1. This means that in use, i.e. with the eye and ophthalmic lens acting together, there is a residual negative longitudinal chromatic aberration. Hence, as shown in FIG. 2, while a green object G at the same position as the green object G in FIG. 1 is sharply focussed on to the eye retina at F, a blue object B has to be further away from the green object G to achieve sharp focussing at F, and a red object R has to be nearer to the eye than the green object G to achieve sharp focussing at F. In other words, the colour order with distance is reversed with the change from positive longitudinal chromatic aberration to negative longitudinal chromatic aberration.

As explained above with reference to FIG. 1, the extent of the positive natural longitudinal chromatic aberration of the eye is about 1 dioptre. In order to more than counteract this, more than about one dioptre of negative longitudinal chromatic aberration is required from the hologram 2. This can be achieved by use of a hologram with a diffractive power of more than about +3.4 dioptres. If it is desired that the extent of the residual negative chromatic effect should be greater than that of the natural positive chromatic effect, then more than about two dioptres of negative longitudinal chromatic aberration is required from the hologram 2. This can be achieved by use of a hologram with a diffractive power of more than about +6.8 dioptres.

It will be understood that the positive (diffractive) lens power of the hologram 2 would by itself add to the natural lens power of a normal eye with which it is associated and thus affect the wearer's vision power. To compensate for this the lens 1 may have negative refractive power of an absolute value the same as that of the positive diffractive power of the hologram 2 so that the powers cancel. The lens then has an overall or residual zero lens power but still retains the chromatic effect.

It will be appreciated, however, that if the eye E in fact requires some corrective power, then the lens 1 may have a refractive power which does not balance the diffractive power of the hologram 2, but the values could be so selected as to give an overall power or to leave a residual power which is that required by the particular eye for correction. For example, a patient with a +5 dioptre refractive error could wear a lens 1 which combines a +7 dioptre diffractive power hologram 2 with a refractive power of −2 dioptres.

If a negative power correction for the eye is required, then the lens 1 could have a negative refractive power which exceeds the positive diffractive power of the hologram 2. If a positive corrective power greater than the positive diffractive power of the hologram 2 is required, then the refractive power of the lens 1 can also be positive so as to add to that of the hologram 2. In the peculiar case where a patient requires a positive corrective power equal to the positive diffractive power of the hologram 2, then the lens 1 can be of zero refractive power.

The ophthalmic lens 1 may take the form of a spectacle lens, or may be a contact lens, or could be an implant lens which is surgically inserted in the eye to replace a defective natural lens L.

In the case of a contact lens (or an implant lens) the hologram 2 would generally extend over the full visually used area of the lens. With a spectacle lens, the hologram 2 may be provided only over a reading portion or near portion, as in a bifocal or progressive lens.

The hologram 2 may be optically generated in or on the lens 1, or may be mechanically generated as a surface relief hologram on or in the lens 1. The hologram may take a form, and/or be generated in a manner, as described in U.K. patent application No. GB 2 101 764A, the relevant teachings of which are incorporated herein by reference.

The refractive power of the lens 1 is provided by refracting faces which are curved when viewed in axial-section (as in FIG. 2 which shows curved anterior and posterior refracting faces 3 and 4) and which may be of spherical curvature. It will be understood that any longitudinal chromatic aberration of the basic refractive lens is very small and has only a slight effect on that of the holographic element.

It will further be understood that the present invention makes particular use of change of power with colour (wavelength), and that references herein to power (whether refractive, diffractive, residual, overall, corrective, etc.) which are not qualified by colour or wavelength are to be understood as applying to green light of wavelength 555 nonometers unless the context indicates otherwise. However, it is required that the introduction of longitudinal chromatic aberration with the diffractive power should occur substantially uniformly across the full continuum of the visible spectrum and with high efficiency. A hologram 2 of as uniformly high efficiency as possible is therefore called for, e.g. an efficiency of more than 50%, and preferably at least 80%, at all wavelengths, and preferably with less than 20% difference between the maximum and minimum efficiencies, across the visible spectrum. The maximum efficiency should preferably be greater than 70%. A particular example of hologram may have a minimum efficiency of about 85% or more at the extremes of the visible spectrum and a maximum efficiency of about 99% or higher at the centre for green light.

It will be appreciated that an ophthalmic lens in accordance with the present invention can be thin, at least at its central portion, since it does not need to provide a high positive refractive power. Even when a high positive corrective power is required by the patient, the positive diffractive power of the lens can generally enable the requirement to be met with a relatively modest positive refractive power. Thinness of the lens is an advantage, particularly in the case of a contact lens, from the aspects of wearer comfort and, where relevant, oxygen transmission. However, the residual longitudinal chromatic aberration, whose extent may be greater than that of the natural chromatic aberration, can enable the eye to perform a variety of tasks without needing to adjust its focus (accommodate).

I claim:

1. An ophthalmic lens having positive diffractive power which introduces negative longitudinal chromatic aberration to an extent that more than counteracts the natural positive longitudinal chromatic aberration of the eye so as to provide in use a residual negative longitudinal chromatic aberration.

2. A lens according to claim 1 whose positive diffractive power is of a magnitude such that the introduced negative longitudinal chromatic aberration has an absolute value greater than twice that of the natural positive longitudinal chromatic aberration of the eye.

3. A lens according to claim 1 whose diffractive power is about $+3.4D$ dioptres where $-D$ is the extent of negative longitudinal chromatic aberration required to be introduced.

4. A lens according to claim 1 having zero refractive power.

5. A lens according to claim 1 having refractive power so that the overall or residual power of the lens is determined by the algebraic sum of the diffractive and refractive powers.

6. A lens according to claim 5 whose refractive power is negative and of a magnitude such as to balance or cancel the diffractive power so that the overall or residual power is substantially zero.

7. A lens according to claim 5 whose refractive power is provided by faces which are curved as viewed in axial section.

8. A lens according to claim 7 in which said faces are of spherical curvature.

9. A contact lens according to claim 1.

10. An implant lens according to claim 1.

11. A lens according to claim 9 having the diffractive power over its full visually used area.

12. A lens according to claim 10 having the diffractive power over its full visually used area.

13. A spectacle lens according to claim 1.

14. A lens according to claim 13 having the diffractive power over part only of the visually used area.

15. A lens according to claim 1 having an efficiency of diffraction of more than 50% at all wavelengths across the visible spectrum.

16. A lens according to claim 15 having a maximum efficiency of diffraction of more than 70%.

17. A lens according to claim 16 having a difference between the maximum and minimum efficiencies of diffraction of less than 20%.

* * * * *